United States Patent
Kado et al.

(12)

(10) Patent No.: US 6,316,032 B1
(45) Date of Patent: *Nov. 13, 2001

(54) BARLEY MALT OIL CONTAINING VEGETABLE CERAMIDE-ASSOCIATED SUBSTANCES AND PROCESS FOR PRODUCING THE SAME

(75) Inventors: Hisao Kado; Fujio Kobayashi, both of Yaizu; Akira Hirota; Naoki Abe, both of Shizuoka, all of (JP)

(73) Assignee: Sapporo Breweries Limited, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,982
(22) PCT Filed: Dec. 24, 1998
(86) PCT No.: PCT/JP98/05855
§ 371 Date: Aug. 23, 1999
§ 102(e) Date: Aug. 23, 1999
(87) PCT Pub. No.: WO99/33939
PCT Pub. Date: Jul. 8, 1999

(30) Foreign Application Priority Data

Dec. 26, 1997 (JP) ..................................... 9-366876

(51) Int. Cl.⁷ ............................ A61K 35/78; A61K 35/00
(52) U.S. Cl. ........................... 424/750; 424/115; 426/28; 426/44; 426/430; 426/436
(58) Field of Search .................................. 424/750, 115; 426/28, 44, 430, 436

(56) References Cited

U.S. PATENT DOCUMENTS

| | | | |
|---|---|---|---|
| 4,804,545 | * | 2/1989 | Goering et al. ........................ 426/28 |
| 5,013,561 | * | 5/1991 | Goering et al. ........................ 426/28 |
| 5,135,765 | * | 8/1992 | Kishi et al. .......................... 426/417 |

FOREIGN PATENT DOCUMENTS

| | | | |
|---|---|---|---|
| 2053182 | * | 5/1991 | (DE) . |
| 3-123479 | * | 5/1991 | (JP) . |
| 5-30981 | * | 2/1993 | (JP) . |
| 1776407 | * | 11/1992 | (SU) . |

* cited by examiner

Primary Examiner—Christopher R. Tate
(74) Attorney, Agent, or Firm—Oblon, Spivak, McClelland, Maier & Neustadt, P.C.

(57) ABSTRACT

The present invention has for its object to provide a method for obtaining a barley malt oil abundantly containing ceramide derivatives of plant origin which is highly safe and gives a good image as a material in an efficient, simple and easy manner as well as to provide a barley malt oil which is obtained by such method above and is enriched in highly safe ceramide derivatives. The present invention provides a method for producing barley malt oil containing ceramide derivatives, comprising the steps of: dipping spent grains obtained in a process of beer production in a polar organic solvent as a dipping solution, separating an extract liquid from the dipping solution, and concentrating the extract liquid and also provides a barley malt oil containing ceramide derivatives obtainable by dipping spent grains obtained in a process of beer production in a polar organic solvent, separating an extract liquid from the resulting solution, and concentrating the extract liquid.

42 Claims, No Drawings

BARLEY MALT OIL CONTAINING VEGETABLE CERAMIDE-ASSOCIATED SUBSTANCES AND PROCESS FOR PRODUCING THE SAME

TECHNICAL FIELD

The present invention relates to barley malt oil containing ceramide derivatives and their production method and more particularly to a barley malt oil containing ceramide derivatives derived from spent grains obtained during the process of beer production and a method for simply and easily producing the barley malt oil.

BACKGROUND ART

From old times, animal oil or vegetable oil has been used in many applications such as for foods, cosmetics, as well as for medicines.

Heretofore, use of such animal and vegetable oils has been directed mainly to applications for improvement of physical properties of foods and cosmetics or as solvents, dispersants, etc., due to their unique physical properties, i.e., liquidity with high viscosity at ambient temperature.

Recently, analysis of many lipid components existing in such animal and vegetable oils has progressed, which revealed that among the lipids, ceramide associated substances such as ceramide and cerebroside (ceramide glycolipids) have a high moisture retention effect. Also, it has come to be known that the ceramide associated substances exist abundantly in the horny layer of human skin and serve to prevent evaporation of moisture from the body.

Further, it has been clarified that the ceramide associated substances have an effect of preventing the penetration of antigens into the body from the outside and function to be effective against atopic dermatitis. Accordingly, development of ceramide associated substances as medical preparations has recently been under way.

Hitherto, the ceramide associated substances have been extracted from brains and spinal marrow of bovine and ever been supplied. However, in view of the possibility that it could cause bovine hydrophobia to infect to humans and from the viewpoint of prevention of cruelty to animals, their supply has been decreased remarkably so that it is demanded to secure raw materials which substitute for them.

Since chemical structure of the ceramide associated substances is already known, their synthetic products have been produced and come to be used as substitutes for the above natural ceramide associated substances.

However, regarding the synthetic products, safety of reactants used for chemical reactions and of impurities such as by-products produced during the reactions has not been established yet.

Therefore, they must be purified to extremely high degrees of purity, which increases their price. Also, it is pointed out that synthetic products are inferior in effect to natural ceramides.

Under the circumstances, there are strongly demanded for ceramide derivatives of a plant origin which are highly safe and moreover give a good image as a material.

As the ceramide derivatives, those derived from rice (Agric. Biol. Chem., 49, 2753 (1985)) and wheat (Agric. Biol. Chem., 49, 3609 (1985)) are well-known and these cereals originated ceramide derivatives have already been under way of development as materials for cosmetics.

However, although such cereals contain ceramide derivatives, their concentration is very low so that their extraction and purification take much time and cost.

An object of the present invention is to overcome the above-described defects of the prior art and provide a method for efficiently, simply and easily obtaining barley malt oil which contains abundant ceramide derivatives of a plant origin that are highly safe and give a good image as a material.

An additional object of the present invention is to provide barley malt oil which is obtained by such methods as above and contains abundantly highly safe ceramide derivatives.

To achieve the above-described objects, the present inventors have made intensive research, during which were focused on spent grains which is a by-product produced quantitatively according as the production of beer proceeds.

More specifically, in the charging step which is conducted first in the production of beer, wort is obtained by filtration of mash after saccharification, during which procedure spent grains is separated and discharged in large amounts as a by-product.

The spent grains, which is generated quantitatively according as beer is produced, is currently utilized mainly as a cattle feed.

However, in accordance with a recent decline of stock-breeding and an increase in importation of feed and stock-breeding products as a result of deregulation, the demand as a feed is in a decreasing tendency. Accordingly, it has become a problem to find new application of spent grains, in place of usage as a cattle feed.

In the process of studying such a method of efficiently utilizing spent grains, the present inventors have found that spent grains can be used very advantageously as a raw material for producing ceramide derivatives.

That is, the present inventors have found that spent grains contains a large amount of lipid (about 10% in a dry matter), in which there is a very large amount of ceramide derivatives which can be used as a material for cosmetics or a material for medicines so that spent grains can be used very advantageously as a raw material for producing ceramide derivatives.

First, spent grains, from which is recovered most of the lipid contained in the raw material for producing beer such as malt, contains a very large amount of lipid as much as about 10% based on the weight of dry matter.

The lipid components in the spent grains include a lot of ceramide derivatives.

Spent grains, a by-product obtained quantitatively according as beer production process, was already heated at the process of wort production so that thermally unstable lipids therein have been decomposed. Also, by the action of lipase which was generated when barley grains germinated, fatty acid esters were hydrolyzed to free fatty acids.

Hitherto, when ceramide derivatives are extracted from cereals such as rice and wheat, it has been necessary to conduct a step of alkali treatment to separate ceramide derivatives from unnecessary materials such as other phospholipid or neutral lipids.

However, use of spent grains instead of rice or wheat as a raw material for ceramide derivatives enables one to eliminate such a step of separation from unnecessary materials so that a lipid fraction which contains ceramide derivatives abundantly can be obtained in a very simple and easy manner.

In addition, spent grains are safe since it is a by-product in food production derived from plants, and can always be supplied with stable quality.

Therefore, spent grains can be used very advantageously as a raw material for producing ceramide derivatives.

The present invention is made based on the above-described findings and is to provide a method for producing ceramide derivatives contained in spent grains in a simple and easy manner.

DISCLOSURE OF THE INVENTION

The present invention as defined as embodiment 1 is to provide a method for producing barley malt oil containing ceramide derivatives, comprising the steps of dipping spent grains obtained in a process of beer production in a polar organic solvent as a dipping solution, separating an extract liquid from said dipping solution, and concentrating said extract liquid.

Next, the invention as defined as embodiment is to provide a method for producing barley malt oil containing ceramide derivatives as described as embodiment 1, wherein a residue obtained in the step of separating the extract liquid from the dipping solution according to the method described as embodiment 1 is dipped in a polar organic solvent and then an extract liquid is separated from said dipping solution, and said extract liquid and the previously obtained extract liquid are mixed and concentrated.

Also, the invention as defined as embodiment 3 is to provide a method for producing barley malt oil containing ceramide derivatives as described as embodiment 1, further comprising the steps of dissolving the concentrate obtained in the concentration step according to the method described as embodiment 1 in a mixed solvent consisting of a halogen-based organic solvent and an alcohol to separate and remove insoluble material, and concentrating the solution obtained in the above separation and removal step.

Further, the invention as defined as embodiment 4 is to provide a method for producing barley malt oil containing ceramide derivatives as described as embodiment 2, further comprising the steps of dissolving the concentrate obtained in the concentration step according to the method described as embodiment 2 in a mixed solvent consisting of a halogen-based organic solvent and an alcohol to separate and remove insoluble material, and concentrating the solution obtained in the above separation and removal step.

Also, the invention as defined as embodiment 5 is to provide a method for producing barley malt oil containing ceramide derivatives as described as embodiment 4, wherein the concentrate obtained in the last concentration step of the method described as embodiment 4 is subjected to a step of solvent fractionation.

Finally, the invention as defined as embodiment 6 is to provide a barley malt oil containing ceramide derivatives obtainable by dipping spent grains obtained in a process of beer production in a polar organic solvent, separating an extract liquid from said resulting solution, and concentrating said extract liquid.

BEST MODE FOR CARRYING OUT THE INVENTION

Hereafter, the present invention will be described in detail.

First, the invention as defined as embodiment 1 will be explained.

The invention as defined as embodiment 1 relates to a method for producing barley malt oil containing vegetable ceramide associated substances and comprises the steps of dipping spent grains obtained in a process of beer production in a polar organic solvent as a dipping solution, separating an extract liquid from said dipping solution, and concentrating said extract liquid.

In the invention as defined as embodiment 1, the spent grains used as a raw material is a by-product produced when wort is obtained in the process of beer production.

Spent grains are produced usually in a state where a large amount of water is contained (water content: about 90%). In the present invention, the spent grains may be of any form; it may be used in a water-containing state (water content: about 90%) as it is or after reducing the water content to about 60 to 65% by a squeezer such as a cylinder press or a filter press, further it may be squeeze spent grains (water content: about 0 to 20%).

When squeezed spent grains is used as a raw material, it is preferred to use spent grains dried by heating at not so high a temperature (e.g., 60 to 100° C.) since drying under the conditions where it is exposed to high temperatures will result in denaturation of the target substance by heat. Further, when drying treatment is performed in a squeezer, there is the possibility that some amount of the target substance may leak together with water and yield may decrease so that it had better use a squeezer less frequently.

Therefore, usually the spent grains as a raw material which is used most preferably is spent grains in a water-containing state just as discharged from the process.

Further, in order to increase yield, it is also possible to previously collect high lipid content portions of a raw material or that is spent grains, and extract them with an alcohol to efficiently obtain the target substance. The high lipid content portions are portions of spent grains that have relatively small granularity so that they can be collected by a conventional method such as filtration using a sieve, rough cloth, paper or the like.

In the present invention as defined as embodiment 1, first the spent grains as a raw material is dipped in a polar organic solvent. By this dipping step, ceramide derivatives, or target substance, can be extracted.

The polar organic solvent used in the dipping step may be any solvent that has polarity such as an alcohol, chloroform, or acetone. In particular, alcohols having high hydrophilicity are preferred.

As the alcohol, there can be used any alcohol that has polarity and is miscible with water, such as methanol, ethanol, propanol, isopropanol, and butanol. However, taking into consideration of production costs or the solvent removing step by concentration as will be described later on, methanol is used most preferably.

Use of hexane or chloroform-methanol mixed solution instead of alcohols is not so preferred since unnecessary lipids are extracted and later purification operations will become complicated.

The amount of the polar organic solvent to be used is not limited particularly. However, if the amount is small, there arises a problem, for example, that filtration operation must be performed under pressure. To enable natural filtration by liquefaction of a mixture of a polar organic solvent and spent grains, it is preferred that the amount of the solvent to be added is more than 3 times as much as the weight of spent grains. On the other hand, the upper limit of the amount of polar organic solvent to be used is not set particularly and it may be added as much as possible if it is economically admissible to.

When an alcohol is used as the polar organic solvent, it is preferred that the alcohol contains water in an amount of about 10 to 20%. It is for this reason that the water-containing spent grains as discharged from the process can be used most advantageously as the raw material for production used in the method of the present invention.

The temperature at the time of dipping (extraction) is preferably as high as possible since the efficiency of extraction of the target substance is improved but the object can be achieved sufficiently when room temperature conditions are employed.

Also, there is no particular limitation on the dipping time. The target substance can be extracted sufficiently by dipping for about 1 to 15 hours. The time required for extraction can be reduced by stirring the solvent.

Then, the extract liquid is separated from the dipping solution. That is, extracted soluble substances are separated from the solution of the polar organic solvent used for dipping.

The method of separation is not limited particularly and separation can be performed by using, for example, a press filter, a cylinder press, a screw decanter, etc.

The extract liquid separated from the dipping solution in this manner is sent to a concentration step.

As described as embodiment 2, it is also possible to dip a residue obtained in the step of separating the extract liquid from the dipping solution again in a polar organic solvent, separate an extract liquid from said dipping solution, mix said extract liquid with the previously obtained extract liquid and send the resulting mixture to a subsequent concentration step. This method can further increase the extraction efficiency.

That is, the extraction efficiency can be increased by dipping spent grains (for example, water-containing spent grains of about 90% water content) in a polar organic solvent in an amount of 3 times or more followed by extraction and extracting the residue obtained in the step of separating the extract liquid again with the same amount of the polar organic solvent.

Next, concentration treatment of the extraction liquid is carried out.

The concentration treatment may be performed using, for example, a rotary evaporator.

As described above, in the case of the present invention as defined as embodiment 2, a residue obtained in the step of separating the extract liquid from the dipping solution is dipped again in a polar organic solvent, an extract liquid is separated from the dipping solution, the extract liquid is mixed with the previously obtained extract liquid and the mixture is subjected to a subsequent concentration step.

As a result of the concentration treatment, a concentrate which is a brown oily substance, i.e., a barley malt oil containing target ceramide derivatives, can be obtained.

The concentrate which is a brown oily substance may further be subjected to additional steps as described below to further increase the purity of the ceramide derivatives.

That is, as described as embodiment 3, there are further performed, in the method as described as embodiment 1, a step of dissolving the concentrate obtained in the concentration step in a mixed solvent consisting of a halogen-based organic solvent and an alcohol to separate and remove insoluble material, and a step of concentrating the solution obtained in the above separation and removal step.

First, the concentrate (oily substance) obtained as described above is dissolved in a mixed solvent of a halogen-based organic solvent-methanol to remove insoluble material so that water-soluble substances such as saccharides and inorganic salts can be removed.

As the halogen-based organic solvent, chloroform, dichloromethane, etc. are effective.

Here, when a mixed solvent of chloroform-methanol is used, it is preferred to use that the mixed solvent has a mixing ratio of chloroform and methanol of 5:5 to 9:1 (volume ratio) in order to sufficiently dissolve ceramide derivatives.

Next, after completion of the step of dissolving the concentrate obtained in the concentration step in a mixed solvent of a halogen-based organic solvent and an alcohol and separating and removing insoluble material as mentioned above, the solution obtained in the above separation and removal step is again subjected to concentration treatment to remove the mixed solvent of a halogen-based organic solvent and an alcohol.

The concentration treatment may be carried out by using, for example, a rotary evaporator as in the preceding concentration treatment.

Further, if needed, the concentrate may be washed with a solvent such as hexane or ether to remove low polarity impurities such as fatty acid esters.

As described as embodiment 4, there can be further performed, in the method as described as embodiment 2, a step of dissolving the concentrate obtained in the concentration step in a mixed solvent consisting of a halogen-based organic solvent and an alcohol to separate and remove insoluble material and a step of concentrating the solution obtained in the separation and removal step.

The concentrate obtained at this point contains 10% or more ceramide derivatives and satisfies the object of the present invention.

However, it still contains relatively high proportions of unnecessary components other than ceramide derivatives and is of high degree of coloring so that it finds a limited application.

Accordingly, by subjecting the concentrate to decoloring treatments singly or in appropriate combinations, unnecessary components can be removed from the concentrate to decrease the degree of coloring so that the purity of ceramide derivatives can be increased.

Examples of the decoloring treatment include solvent fractionation, treatment with activated carbon, treatment with a hydrophobic resin, etc.

First, the solvent fractionation is a method which decreases the degree of coloring by utilizing a difference in solubility in the solvent between the target substance and coloring components.

The solvent used here may be any solvent so far as the target substance is insoluble therein but the coloring components are soluble therein and the alcohols used in the extraction as described above can be used preferably. In addition, it is also possible to use other solvents such as acetone and ethyl acetate singly or as appropriate mixtures.

For example, the solvent fractionation is carried out by adding methanol to the concentrate, mildly heating the mixture to solubilize the target substance, filtering the solution while it is hot to remove insoluble material, slowly lowering the temperature and finally leaving the solution to stand at 0° C. or less for several hours to several days to deposit pale yellow precipitates. Thus, the degree of coloring can be decreased to increase the purity of the ceramide derivatives.

Next, the treatment with activated carbon, a hydrophobic resin, or the like is more specifically a treatment wherein a solution of the target substance dissolved in a solvent such as a mixed solvent of chloroform-methanol (chloroform:methanol=2:1) is poured in a column packed with activated carbon or a hydrophobic resin to have coloring substances absorbed thereon, or instead, to have the target substance adsorbed thereon.

As the carrier for the resin treatment, there can be used hydrophobic resins such as Amberlite HP series resins advantageously.

Further, depending on the purpose of use, the purity of ceramide derivatives can be further increased by means of chromatography using a silica gel column and/or fractionating high performance liquid chromatography.

As described above, a barley malt oil containing ceramide derivatives can be obtained.

It is the present invention as defined as embodiment 6 that provides such a barley malt oil containing ceramide derivatives.

That is, the present invention as defined as embodiment 6 is to provide a barley malt oil containing ceramide derivatives obtainable by dipping spent grains obtained in a process of beer production in a polar organic solvent, separating an extract liquid from the resulting solution, and concentrating said extract liquid, and more specifically obtainable by the present invention as defined as embodiment 1. Therefore, the kind of polar organic solvent and conditions of dipping, for example, are the same as described in the description relative to the present invention as defined as embodiment 1.

The present invention as defined as embodiment 6 may include the barley malt oil containing ceramide derivatives obtainable by the present invention as defined as embodiments 2 to 5.

The barley malt oil described as embodiment 6 thus obtained contains ceramide derivatives abundantly (10% by weight or more of the total), and its purity can be increased up to about 90% by repeating purification and fractionation.

The thus obtained ceramide associated substances derived from spent grains have chemical structures similar to those of ceramide associated substances derived from other plants such as wheat and rice and are equivalent thereto in moisture retention effect, etc., so that they can be used as a raw material for cosmetics by blending them in cream, milky lotion, etc. Further, they can be used as a raw material for medicines.

Hereafter, the present invention will be described concretely by way of examples. However, the present invention should not be limited thereto.

EXAMPLE 1

To 1 kg of spent grains (water content: 90%) discharged from beer factory was added 9 L (liters) of methanol and stirred at room temperature for 24 hours. Thereafter, the mixture was separated into an extract liquid and a residue by filtration through a gauze and centrifugation. To the residue was added 8 L of methanol to extract again.

The first and second extract liquids were combined and concentrated in a rotary evaporator to obtain 8.7 g of a concentrate (lipid) from 1 kg of spent grains.

The total amount of the concentrate was dissolved in a mixed solvent of chloroform-methanol (chloroform : methanol=2:1) and filtered to remove insoluble material.

Again a rotary evaporator was used for concentration to remove the solvent and then the concentrate was washed with n-hexane and dried to obtain 6.5 g of brown powder. Table 1 shows the purity of ceramide derivatives in the obtained powder.

EXAMPLE 2

A 5 g portion out of the brown powder of Example 1 was dissolved in a mixed solvent of chloroform-methanol (2:1) and charged in a silica gel column which was sufficiently stabilized (equilibrated) with flowing chloroform in advance and the column was washed with chloroform to remove low polarity substances.

Thereafter, the solvent was changed to a mixed solvent of chloroform-methanol (8:2) to elute the adsorbed substances.

The eluted fractions were collected and the solvent was removed therefrom with a rotary evaporator to obtain 2.4 g of pale brown powder. Table 1 shows the purity of ceramide derivatives in the obtained powder.

EXAMPLE 3

A 0.5 g portion out of the pale brown powder of Example 2 was dissolved in 5 mL of a mixed solvent of chloroform-methanol (2:1) and charged in the same silica gel column as used in Example 2 which was sufficiently stabilized (equilibrated) with flowing a mixed solvent of chloroform-methanol (9:1) in advance.

The eluates were fractionated in fixed amount portions and the fractions which showed the existence of ceramide derivatives by silica gel thin layer chromatography were collected and the solvent was removed therefrom with a rotary evaporator.

This operation gave 0.21 g of pale yellow powder. Table 1 shows the purity of ceramide derivatives in the obtained powder.

EXAMPLE 4

A 0.1 g portion out of the pale yellow powder of Example 3 was dissolved in 0.5 mL of a mixed solvent of chloroform-methanol (2:1) and purified by high performance liquid chromatograph system using a silica gel column and then further purified by normal phase chromatography using a mixed solvent of hexane-methanol as an eluent.

The eluates from the column was monitored by an ultraviolet ray detector at a wavelength of 205 nm and peak fractions were collected, subjected to thin layer chromatography to collect ceramide derivatives, and the solvent was removed with a rotary evaporator.

This operation gave 0.07 g of dim yellow powder. Table 1 shows the purity of ceramide derivatives in the obtained powder.

EXAMPLE 5

A 1 g portion out of the brown powder of Example 1 was charged in methanol warmed to about 60° C. with stirring. While retaining the same temperature as above, the mixture was filtered with a filter paper to remove insoluble material and then the temperature was slowly lowered to −20° C. at which temperature the filtrate was left to stand over one night. The precipitates formed were collected and charged again in methanol warmed to about 60° C., followed by the same operation as above.

After the second operation, the obtained precipitates were dried to obtain 0.11 g of pale yellow powder. Table 1 shows the purity of ceramide derivatives in the obtained powder.

TABLE 1

|  | Example 1 | Example 2 | Example 3 | Example 4 | Example 5 |
| --- | --- | --- | --- | --- | --- |
| Appearance | Brown | Pale brown | Pale yellow | White to dim yellow | Pale yellow |
| Purity of ceramide derivatives | 11% | 23% | 60% | 91% | 58% |

According to the present invention as defined as embodiment 1, a barley malt oil abundantly containing ceramide derivatives of plant origin which is highly safe and gives a good image as a material can be obtained efficiently.

That is, the spent grains as a raw material is a by-product in production of foods of plant origin and hence it is safe and it can always be supplied with a stable quality.

Further, the step of separating ceramide derivatives from other lipids (such as alkali treatment) which is necessary for extracting ceramide derivatives from other cereals can be eliminated. Therefore, lipid fractions enriched in ceramide derivatives can be obtained in a very simple and easy manner.

Further, as in the present invention as defined as embodiments 2 to 5, addition of additional steps makes it possible to obtain efficiently a barley malt oil containing more abundantly ceramide derivatives of plant origin which is highly safe and gives a good image as a material.

Furthermore, according to the invention as defined as embodiment 6, a barley malt oil abundantly containing highly safe ceramide derivatives can be obtained.

Also, by the method of the present invention as defined as embodiment 1 to 5, after a barley malt oil containing ceramide derivatives is obtained from spent grains, the residue does not have to be disposed but can be reused as a material for foods such as food fiber or long-term storage feed.

That is, hitherto, there has been a problem in utilization of spent grains that odor is generated according as lipids are deteriorated. However, when ceramide derivatives (lipids) are produced from spent grains by the method of the present invention as defined as embodiments 1 to 5, the spent grains after removal of such substances is free of the odor which otherwise accompanies the deterioration of lipids. Therefore, even after useful ceramide derivatives are obtained from spent grains, the residue does not have to be disposed of but can be utilized advantageously as a material for foods such as food fiber or long-term storage feed.

Industrial Applicability

The present invention can be utilized effectively in the field such as cosmetics production and medicine production.

What is claimed is:

1. A method for producing a concentrate of barley malt oil containing ceramides, consisting essentially of the steps of:

dipping barley spent grains having a water content of more than 20% (obtained in a process of beer production) in a polar organic solvent as a dipping solution, separating said dipping solution into an extract liquid and a residue concentrating said extract liquid to obtain a concentrate of barley malt oil, and recovering the concentrate of barley malt oil.

2. The method for producing a concentrate of barley malt oil containing ceramides as claimed in claim 1, wherein the residue obtained in the step of separating the dipping solution into the extract liquid and the residue is dipped in a polar organic solvent, and then an extract liquid is separated from said dipping solution, the thus obtained extract liquid is recovered, said extract liquid and the previously obtained extract liquid are mixed and concentrated, and the concentrate is recovered.

3. The method for producing a concentrate of barley malt oil containing ceramides as claimed in claim 2, wherein alcohol miscible with water, chloroform or acetone is used as the polar organic solvent.

4. The method for producing a concentrate of barley malt oil containing ceramides as claimed in claim 3, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

5. The method for producing a concentrate of barley malt oil containing ceramides as claimed in claim 4, wherein chloroform is used as the halogen-based organic solvent and the mixing ratio of said chloroform to said alcohol is from 5:5 to 9:1 (volume ratio).

6. The method for producing a concentrate of barley malt oil containing ceramides as claimed in claim 5, wherein the recovered concentrate is subjected to a step of solvent fractionation.

7. The method for producing a concentrate of barley malt oil containing ceramides as claimed in claim 4, wherein the recovered concentrate is subjected to a step of solvent fractionation.

8. The method for producing a concentrate of barley malt oil containing ceramides as claimed in claim 2, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

9. The method for producing a concentrate of barley malt oil containing ceramides as claimed in claim 8, wherein chloroform is used as the halogen-based organic solvent and the mixing ratio of said chloroform to said alcohol is from 5:5 to 9:1 (volume ratio).

10. The method for producing a concentrate of barley malt oil containing ceramides as claimed in claim 9, wherein the recovered concentrate is subjected to a step of solvent fractionation.

11. The method for producing a concentrate of barley malt oil containing ceramides as claimed in claim 8, wherein the recovered concentrate is subjected to a step of solvent fractionation.

12. The method for producing a concentrate of barley malt oil containing ceramides as claimed in claim 1, wherein alcohol miscible with water, chloroform or acetone is used as the polar organic solvent.

13. The method for producing a concentrate of barley malt oil containing ceramides as claimed in claim 12, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

14. The method for producing a concentrate of barley malt oil containing ceramides as claimed in claim 13, wherein chloroform is used as the halogen-based organic solvent and the mixing ratio of said chloroform to said alcohol is from 5:5 to 9:1 (volume ratio).

15. The method for producing a concentrate of barley malt oil containing ceramides as claimed in claim 14, wherein the recovered concentrate is subjected to a step of solvent fractionation.

16. The method for producing a concentrate of barley malt oil containing ceramides as claimed in claim 13, wherein the recovered concentrate is subjected to a step of solvent fractionation.

17. The method for producing a concentrate of barley malt oil containing ceramides as claimed in claim 1, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

18. The method for producing a concentrate of barley malt oil containing ceramides as claimed in claim 17, wherein the recovered concentrate is subjected to a step of solvent fractionation.

19. The method for producing a concentrate of barley malt oil containing ceramides as claimed in claim 17, wherein chloroform is used as the halogen-based organic solvent and the mixing ratio of said chloroform to said alcohol is from 5:5 to 9:1 (volume ratio).

20. The method for producing a concentrate of barley malt oil containing ceramides as claimed in claim 19, wherein the recovered concentrate is subjected to a step of solvent fractionation.

21. The method for producing a concentrate of barley malt oil containing ceramides as claimed in claim 1, wherein the concentrate is recovered without an alkali treatment.

22. A method for producing a concentrate of barley malt oil containing ceramides, consisting essentially of the steps of:

dipping dry barley spent grains in a polar organic solvent as a dipping solution, separating said dipping solution into an extract liquid and a residue, concentrating said extract liquid to obtain a concentrate of barley malt oil, and recovering the concentrate of barley malt oil.

23. The method for producing a concentrate of barley malt oil containing ceramides as claimed in claim 22, wherein the residue obtained in the step of separating the dipping solution into the extract liquid and the residue is dipped in a polar organic solvent, and then an extract liquid is separated from said dipping solution, the thus obtained extract liquid is recovered, said extract liquid and the previously obtained extract liquid are mixed and concentrated, and the concentrate is recovered.

24. The method for producing a concentrate of barley malt oil containing ceramides as claimed in claim 23, wherein alcohol miscible with water, chloroform or acetone is used as the polar organic solvent.

25. The method for producing a concentrate of barley malt oil containing ceramides as claimed in claim 24, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

26. The method for producing a concentrate of barley malt oil containing ceramides as claimed in claim 25, wherein chloroform is used as the halogen-based organic solvent and the mixing ratio of said chloroform to said alcohol is from 5:5 to 9:1 (volume ratio).

27. The method for producing a concentrate of barley malt oil containing ceramides as claimed in claim 26, wherein the recovered concentrate is subjected to a step of solvent fractionation.

28. The method for producing a concentrate of barley malt oil containing ceramides as claimed in claim 25, wherein the recovered concentrate is subjected to a step of solvent fractionation.

29. The method for producing a concentrate of barley malt oil containing ceramides as claimed in claim 23, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

30. The method for producing a concentrate of barley malt oil containing ceramides as claimed in claim 29, wherein chloroform is used as the halogen-based organic solvent and the mixing ratio of said chloroform to said alcohol is from 5:5 to 9:1 (volume ratio).

31. The method for producing a concentrate of barley malt oil containing ceramides as claimed in claim 30, wherein the recovered concentrate is subjected to a step of solvent fractionation.

32. The method for producing a concentrate of barley malt oil containing ceramides as claimed in claim 29, wherein the recovered concentrate is subjected to a step of solvent fractionation.

33. The method for producing a concentrate of barley malt oil containing ceramides as claimed in claim 22, wherein alcohol miscible with water, chloroform or acetone is used as the polar organic solvent.

34. The method for producing a concentrate of barley malt oil containing ceramides as claimed in claim 33, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

35. The method for producing a concentrate of barley malt oil containing ceramides as claimed in claim 34, wherein chloroform is used as the halogen-based organic solvent and the mixing ratio of said chloroform to said alcohol is from 5:5 to 9:1 (volume ratio).

36. The method for producing a concentrate of barley malt oil containing ceramides as claimed in claim 35, wherein the recovered concentrate is subjected to a step of solvent fractionation.

37. The method for producing a concentrate of barley malt oil containing ceramides as claimed in claim 34, wherein the recovered concentrate is subjected to a step of solvent fractionation.

38. The method for producing a concentrate of barley malt oil containing ceramides as claimed in claim 22, further comprising the steps of dissolving the concentrate obtained in the concentration step in a mixed solvent consisting of a halogen-based organic solvent and an alcohol to separate and remove insoluble material, recovering the thus obtained solution, concentrating the thus obtained solution to obtain a concentrate and recovering the concentrate.

39. The method for producing a concentrate of barley malt oil containing ceramides as claimed in claim 38, wherein the recovered concentrate is subjected to a step of solvent fractionation.

40. The method for producing a concentrate of barley malt oil containing ceramides as claimed in claim 38, wherein chloroform is used as the halogen-based organic solvent and the mixing ratio of said chloroform to said alcohol is from 5:5 to 9:1 (volume ratio).

41. The method for producing a concentrate of barley malt oil containing ceramides as claimed in claim 40, wherein the recovered concentrate is subjected to a step of solvent fractionation.

42. The method for producing a concentrate of barley malt oil containing ceramides as claimed in claim 22, wherein the concentrate is recovered without an alkali treatment.

* * * * *